US009682896B2

(12) United States Patent
Ishibashi

(10) Patent No.: US 9,682,896 B2
(45) Date of Patent: *Jun. 20, 2017

(54) PRODUCTION METHOD FOR OLEFIN, AND DEHYDRATION CATALYST EMPLOYED IN SAME

(71) Applicant: Mitsui Chemicals, Inc., Tokyo (JP)

(72) Inventor: Masayasu Ishibashi, Yamaguchi (JP)

(73) Assignee: MITSUI CHEMICALS, INC., Tokyo (JP)

( * ) Notice: Subject to any disclaimer, the term of this patent is extended or adjusted under 35 U.S.C. 154(b) by 12 days.

This patent is subject to a terminal disclaimer.

(21) Appl. No.: 14/896,058

(22) PCT Filed: Jun. 3, 2014

(86) PCT No.: PCT/JP2014/064708
§ 371 (c)(1),
(2) Date: Dec. 4, 2015

(87) PCT Pub. No.: WO2014/196517
PCT Pub. Date: Dec. 11, 2014

(65) Prior Publication Data
US 2016/0122257 A1 May 5, 2016

(30) Foreign Application Priority Data
Jun. 7, 2013 (JP) .................................. 2013-120641

(51) Int. Cl.
*C07C 1/24* (2006.01)
*B01J 21/04* (2006.01)
*B01J 21/08* (2006.01)
*B01J 35/10* (2006.01)
*B01J 21/12* (2006.01)
*B01J 35/02* (2006.01)

(52) U.S. Cl.
CPC .................. *C07C 1/24* (2013.01); *B01J 21/04* (2013.01); *B01J 21/08* (2013.01); *B01J 21/12* (2013.01); *B01J 35/023* (2013.01); *B01J 35/1061* (2013.01); *C07C 2521/12* (2013.01); *Y02P 20/52* (2015.11)

(58) Field of Classification Search
CPC ....... C07C 1/24; C07C 11/06; C07C 2521/12; B01J 21/04; B01J 21/08; B01J 21/12; B01J 35/023; B01J 35/1061
See application file for complete search history.

(56) References Cited

U.S. PATENT DOCUMENTS 5,017,729 A 5/1991 Fukuhara et al.
9,067,199 B2* 6/2015 Nesterenko ............. B01J 29/06

FOREIGN PATENT DOCUMENTS

| JP | 02-006414 | 1/1990 |
| JP | 02-174737 | 7/1990 |
| JP | 03-041035 | 2/1991 |
| JP | 09-030809 | 2/1997 |

OTHER PUBLICATIONS

Akazaki, et al. TOSOH Research & Technology Review, vol. 45, 2001, pp. 65-69.
Experimental Chemistry, vol. 9, 1958, pp. 512-515.
International Search Report mailed Jul. 15, 2014 in PCT/JP2014/064708 (2 pgs.).

* cited by examiner

*Primary Examiner* — Sharon Pregler
(74) *Attorney, Agent, or Firm* — Foley & Lardner LLP

(57) ABSTRACT

An object of the present invention is to provide a method of producing a corresponding olefin such as propylene with a high activity and a high selectivity even in a high LHSV range by an intramolecular dehydration reaction of an alcohol such as isopropyl alcohol. The present invention provides a method of producing an olefin represented by General Formula (II) below from an alcohol represented by General Formula (I) below, which method uses, as a dehydration catalyst, a chemically treated silica gel (X) in which an aluminum compound is supported onto a silica gel (A) with an average fine pore diameter of 10 to 50 nm in the amount of 1,000 to 10,000 ppm by weight in terms of aluminum element. (In General Formulae (I) and (II), $R^1$ is selected from alkyl groups of 1 to 5 carbon atoms and $R^2$ is selected from a hydrogen atom and alkyl groups of 1 to 5 carbon atoms.)

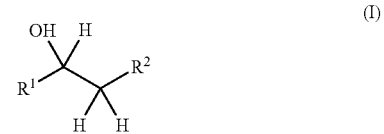

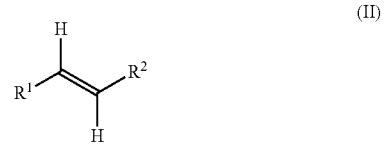

7 Claims, No Drawings

PRODUCTION METHOD FOR OLEFIN, AND DEHYDRATION CATALYST EMPLOYED IN SAME

TECHNICAL FIELD

The present invention relates to a method of producing an olefin with high efficiency by a dehydration reaction of alcohol, and a dehydration catalyst used for the method. In particular, the present invention relates to a method of producing propylene by an intramolecular dehydration reaction of isopropyl alcohol, and a dehydration catalyst used for the method.

BACKGROUND ART

A method of producing cumene by reacting benzene with propylene, a method of producing cumene hydroperoxide by oxidizing cumene, and a method of producing phenol and acetone by subjecting cumene hydroperoxide to acid cleavage are each already known. A method of a combination of these reactions is a method for producing phenol generally called the cumene process and is currently a mainstream method for the production of phenol.

The cumene process has a characteristic of producing acetone simultaneously. This simultaneous production is advantageous when both phenol and acetone are demanded. However, if the amount of the acetone simultaneously produced is in excess of demand, the economic efficiency can be deteriorated due to the price difference between acetone and propylene which is a raw material. In view of this, methods have been then proposed in which the acetone simultaneously produced is converted into propylene through various approaches and is reused as a raw material in the cumene process.

Acetone is readily hydrogenated to be converted into isopropyl alcohol. A process has been proposed in which the thus obtained isopropyl alcohol is dehydrated into propylene and the propylene is reacted with benzene to give cumene. That is, acetone is reused as a material in the cumene process by being converted into propylene through reactions in two stages (Patent Documents 1 and 2). However, such a process may in some cases cause a phenomenon where the reaction activity and the propylene selectivity deteriorate sharply when LHSV (liquid hourly space velocity) is increased at the time of the dehydration reaction of isopropyl alcohol. Developments of techniques for the dehydration reaction from isopropyl alcohol to propylene with a higher productivity have been demanded from industry. Further, the use of a general dehydration catalyst may concurrently induce other reactions such as the oligomerization reaction of formed propylene to thereby produce impurities as by-products; and the selectivity decreases, which is problematic.

CITATION LIST

Patent Literature

Patent Document 1: Japanese Patent Application Laid-Open Publication No. H2-174737
Patent Document 2: Japanese Patent Application Laid-Open Publication No. H3-041035

SUMMARY OF THE INVENTION

Technical Problem

An object of the present invention is to provide a dehydration catalyst whereby a dehydration reaction of alcohol progresses with high efficiency. In particular, an object of the present invention is to provide a method of producing a corresponding olefin by an intramolecular dehydration reaction of alcohol with a high activity and a high selectivity even in a high LHSV range, especially, a method of producing propylene by an intramolecular dehydration reaction of isopropyl alcohol with a high activity and a high selectivity even in a high LHSV range.

Solution to Problem

In order to solve the above-mentioned problem, the present inventors intensively studied to find out that the above-mentioned problem can be solved by using a dehydration catalyst that satisfy particular characteristics, thereby achieving the present invention. That is, the following is the outline of the present invention.

[1] An olefin production method, comprising producing an olefin represented by General Formula (II) below from an alcohol represented by General Formula (I) below using, as a dehydration catalyst, a chemically treated silica gel (X) in which an aluminum compound is supported onto a silica gel (A) with an average fine pore diameter of 10 to 50 nm in an amount of 1,000 to 10,000 ppm by weight in terms of aluminum element:

[Chem. 1]

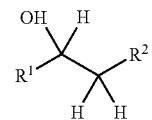

(I)

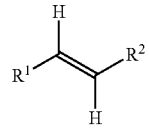

(II)

(in General Formulae (I) and (II), $R^1$ is selected from alkyl groups of 1 to 5 carbon atoms and $R^2$ is selected from a hydrogen atom and alkyl groups of 1 to 5 carbon atoms).

[2] The olefin production method according to [1], wherein
the average fine pore diameter of the silica gel (A) is 20 to 50 nm and
the amount of the aluminum compound supported is more than 1,000 ppm by weight and not more than 10,000 ppm by weight in terms of aluminum element.

[3] The production method according to [1] or [2], wherein the alcohol represented by the General Formula (I) is, in a form of a hydrous alcohol, subjected to a dehydration reaction in the presence of the dehydration catalyst.

[4] The production method according to [3], wherein a content of water in the hydrous alcohol is 1 to 10% by weight.

[5] The olefin production method according to any of [1] to [4], wherein the chemically treated silica gel (X) is a silica gel obtained by bringing the silica gel (A) into contact with a water-soluble aluminum compound and calcining the resulting product.

[6] The olefin production method according to any of [1] to [5], wherein the alcohol represented by General Formula (I) is isopropyl alcohol and the olefin represented by General Formula (II) is propylene.

[7] The olefin production method according to any of [1] to [6], wherein the dehydration reaction temperature is 50 to 500° C.

[8] A dehydration catalyst used for propylene production, comprising a chemically treated silica gel (X) in which an aluminum compound is supported onto a silica gel (A) with an average fine pore diameter of 20 to 50 nm in an amount of more than 1,000 ppm by weight and not more than 10,000 ppm by weight in terms of aluminum element, wherein the propylene production is carried out by a dehydration reaction of hydrous isopropyl alcohol.

Effect of the Invention

According to the production method and the dehydration catalyst of the present invention, an olefin can be produced in a dehydration reaction of alcohol with a high efficiency, that is, with a high alcohol conversion and a high olefin selectivity even in a high LHSV range.

MODE FOR CARRYING OUT THE INVENTION

The present invention will now be described in detail below.

[Olefin Production Method]

The present invention is a method of producing an olefin represented by General Formula (II) below from an alcohol represented by General Formula (I) below, the method using, as a dehydration catalyst, a chemically treated silica gel (X) in which an aluminum compound is supported onto a silica gel (A) with an average fine pore diameter of 10 to 50 nm in the amount of 1,000 to 10,000 ppm by weight in terms of aluminum element. In other words, this production method can be regarded as a production method of an olefin represented by General Formula (II) below, comprising the step of carrying out a dehydration reaction of an alcohol represented by General Formula (I) below in the presence of a dehydration catalyst composed of a chemically treated silica gel (X), wherein the chemically treated silica gel (X) is one in which an aluminum compound is supported onto a silica gel (A) with an average fine pore diameter of 10 to 50 nm, wherein the amount of the aluminum compound supported in the chemically treated silica gel (X) is in a range of 1,000 ppm by weight to 10,000 ppm by weight in terms of aluminum element.

[Chem. 2]

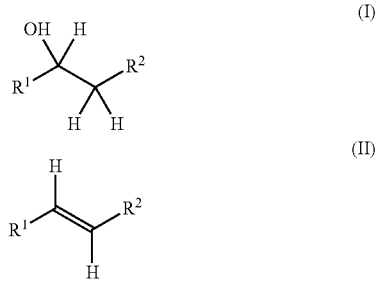

In the above-mentioned General Formulae (I) and (II), $R^1$ is selected from alkyl groups of 1 to 5 carbon atoms and $R^2$ is selected from a hydrogen atom and alkyl groups of 1 to 5 carbon atoms.

The term "dehydration" in the present invention is defined as a reaction in which a hydrogen atom on one carbon atom and a hydroxyl group on another carbon atom are removed as a water molecule, wherein the carbon atoms are adjacent to each other within the same molecule; and all terms having this term as a prefix or a suffix are defined to have the same meaning. In the present invention, the term "dehydration" may in some cases be referred to also as "intramolecular dehydration".

<Raw Material Alcohol and Produced Olefin>

In the olefin production method according to the present invention, a "chemically treated silica gel (X)" is used as a dehydration catalyst to carry out this dehydration reaction of alcohol. Here, the dehydration reaction of an alcohol represented by General Formula (I) below is performed, specifically, in a way that a hydroxyl group and a hydrogen atom located at a position adjacent to the carbon binding to such a hydroxyl group (β position) are eliminated to yield an olefin represented by General Formula (II) below.

[Chem. 3]

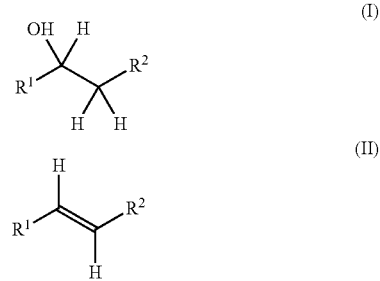

In the above-mentioned General Formulae (I) and (II), $R^1$ is selected from alkyl groups of 1 to 5 carbon atoms and $R^2$ is selected from a hydrogen atom and alkyl groups of 1 to 5 carbon atoms.

Here, examples of the alkyl groups of 1 to 5 carbon atoms can include a methyl group, an ethyl group, an n-propyl group, an isopropyl group, an n-butyl group, an s-butyl group, a t-butyl group, and an n-amyl group. As described later, it is preferred that $R^1$ is a methyl group and $R^2$ is a hydrogen atom in the above-mentioned General Formulae (I) and (II) from the perspective that isopropyl alcohol obtained by a hydrogenation reaction of acetone simultaneously produced in the cumene process can be dehydrated to be applied directly to a process of reproducing propylene which is a raw material of the cumene process. In other words, suitable examples of the alcohol represented by General Formula (I) used in the present invention include an alcohol with $R^1$ being a methyl group and $R^2$ being a hydrogen atom, namely, isopropyl alcohol. In this case, isopropyl alcohol will be converted to a corresponding olefin represented by General Formula (II), namely, propylene by a dehydration reaction.

<Silica Gel (X)>

In accordance with the olefin production method according to the present invention, a chemically treated silica gel (X) is used as a dehydration catalyst. From another point of view, it can be said that the dehydration catalyst used in the present invention is a dehydration catalyst composed of the "chemically treated silica gel (X)".

Here, the silica gel (X) is a chemically treated silica gel in which an aluminum compound is supported onto a silica gel (A) with an average fine pore diameter of 10 to 50 nm in the amount of 1,000 to 10,000 ppm by weight in terms of aluminum element, preferably 1,000 to 5,000 ppm by weight, and more preferably 1,500 to 5,000 ppm by weight. More technically speaking, the silica gel (X) used in the present invention is a chemically treated silica gel in which an aluminum compound is supported onto a silica gel (A) with an average fine pore diameter of 10 to 50 nm in the amount of 1,000 to 10,000 ppm by weight in terms of aluminum element, preferably more than 1,000 ppm by weight and not more than 10,000 ppm by weight, more preferably more than 1,000 ppm by weight and not more than 5,000 ppm by weight, more preferably 1,500 to 5,000 ppm by weight, and still more preferably 2,000 to 3,000 ppm by weight from the viewpoint of a high activity and a high selectivity.

It is to be noted that, in the present invention, the amount of the aluminum compound supported onto the silica gel (A) is expressed in terms of aluminum element. Specifically, the amount of the aluminum compound supported is expressed not as the amount of the aluminum compound in the silica gel (X) but as the content of aluminum element contained in the aluminum compound that is subjected to the support. In addition, when the term "ppm by weight" is used in relation to the aluminum compound, it refers to a proportion of the content of the aluminum element contained in the aluminum compound that is subjected to the support to the weight of the entire silica gel (X).

Silica Gel (A)

A silica gel (A) with an average fine pore diameter of 10 to 50 nm is not in particular restricted as long as it is commonly used as an adsorbent; and examples thereof include ones with an average fine pore diameter of 10 to 50 nm, and preferably more than 10 nm and not more than 50 nm among all of the silica gels produced by six methods described on page 513 of Experimental Chemistry vol. 9, Synthesis and purification of inorganic compound (published Dec. 20, 1958, Maruzen Company, Limited). Yet, from the point of view of reducing oligomerized impurities, a silica gel with an average fine pore diameter of 20 to 50 nm is preferred as such a silica gel (A). For example, a silica gel with an average fine pore diameter of 30 to 50 nm is preferred. In addition, silica gels with a specific surface area of 50 to 900 $m^2/g$ and a fine pore volume of 0.3 to 1.8 ml/g are preferred as the silica gel (A) used in the present invention. Of these, silica gels with a specific surface area of 50 to 200 $m^2/g$ and a fine pore volume of 0.7 to 1.8 ml/g are more preferred. The appropriate size of the average fine pore diameter facilitates diffusion of the formed olefin at the active site of fine pore; and thereby, by-production of oligomers, which are impurities at the active site of fine pore, can presumably be inhibited. These silica gels can be prepared by known methods (for example, Japanese Patent Application Laid-Open Publication No. H9-30809, and Akazaki et al., Tosoh research & technology review, volume 45, 65-69 (2001)); or commercially-available products can be used as well. Examples of such commercially-available products include CARiACT which is a silica for catalyst carrier manufactured by Fuji Silysia Chemical Ltd., and used in the examples described later.

Here, with regard to the kind of silica gel used as the silica gel (A), it may be a crystalline silica gel or may be an amorphous silica gel. Yet, when a crystalline silica gel is used as the silica gel (A), the acid strength of the obtained dehydration catalyst may be too strong. In that case, olefins obtained by the dehydration reaction such as propylene are easy to be oligomerized; and, as a result, the selectivity to olefin tends to decrease. On the other hand, when an amorphous silica gel is used, such oligomerization is likely hard to take place, which tends to be advantageous in terms of increasing the selectivity to olefin. Therefore, as for the kind of silica gel, the amorphous one is preferred.

Aluminum Compound

The chemically treated silica gel (X) used as a dehydration catalyst in the present invention is, as described above, one in which an aluminum compound is supported onto the above silica gel (A) at the proportion stated above in terms of aluminum element.

The aluminum compound supported onto the silica gel (A) contains aluminum as a constituent metal element. Yet, silica gel (A) itself may further contain, as other metal elements, metal elements derived from impurities that are contained in a commercially-available silica in an extremely small amount. For example, the silica gel (A) may contain Ca, Fe, Mg, Na, Ti, or Zr.

The aluminum compound only needs to be water-soluble; and examples thereof include aluminum nitrate, aluminum sulphate, aluminum phosphate, and aluminum perchlorate.

In the present invention, "chemical treatment" is defined as bringing a raw material silica gel into contact with a water-soluble aluminum compound. Here, the above-mentioned water-soluble aluminum compound is usually used as an aqueous solution containing aluminum compound. Further, the above-mentioned contact is usually carried out by solid-liquid contact. Specifically, the silica gel (X) according to the present invention is prepared by subjecting the silica gel (A) to a solid-liquid contact treatment with the above-mentioned aqueous solution.

Here, in the silica gel (X), the aluminum compound may be the same as or may be a different one from the aluminum compound used for support. For example, as describe later, in cases where the silica gel (X) is obtained by bringing the above silica gel (A) into contact with a water-soluble aluminum compound and then calcining the resulting product, all or part of the water-soluble aluminum compound may be decomposed to give a second aluminum compound which is different from the water-soluble aluminum compound in the process of calcination or the like. In that case, the silica gel (X) may eventually contain such a second aluminum compound as the aluminum compound, which is allowed in the production method of the present invention.

Form and Preparation of Silica Gel (X)

In the present invention, a chemically treated silica gel (X) is a silica gel obtained by subjecting the above silica gel (A) to a "chemical treatment" with an aluminum compound. More specifically, the chemically treated silica gel (X) is preferably a silica gel obtained by bringing the above silica gel (A) into contact with a water-soluble aluminum compound and then calcining the resulting product.

When the silica gel (X) is prepared, the preparation is carried out by, for example, a method including bringing the silica gel (A) into contact with an aqueous solution of a water-soluble aluminum compound and then carrying out distillation of water, drying, and calcination; or a known method including impregnating a silica gel with an aqueous solution of water-soluble aluminum compound, wherein the volume of the solution corresponds to the volume of fine pores of the silica gel, and then carrying out drying and calcination. More specifically, the former method is a method including bringing the above-mentioned silica gel (A) into contact to mix with aluminum nitrate which is used as a water-soluble aluminum compound in a mode of low-concentration aqueous solution and then carrying out removal of water under reduced pressure, drying at 120° C., and calcination at 500° C.; and the latter method is a method in which an aqueous aluminum nitrate solution is mixed with the silica gel (A) to be impregnated in the fine pore, wherein the amount of the solution corresponds to the volume of the fine pore of the silica gel (A), and then carrying out drying at 120° C. and calcination at 500° C. The latter method is preferably employed because the water distillation operation is not required and the steps are thus simplified. In the examples of the present invention, the latter method is employed. It is to be noted that, as described above, the calcination at a high temperature such as 500° C. is preferred because such calcination often changes the surface conditions and leads to inhibition of side reactions.

A shape of the chemically treated silica gel (X) as the dehydration catalyst according to the present invention is not in particular restricted, and any of spherical form, cylindrical form, extruded form, and crushed form may be used. In addition, the size of the particle may be in a range of 0.01 mm to 100 mm and selected as appropriate according to the size of reactor.

<Conditions in which Dehydration Reaction is Carried Out>

In the olefin production method according to the present invention, a dehydration reaction of the above-mentioned alcohol represented by General Formula (I) is carried out in the presence of the above dehydration catalyst.

In the present invention, the above-mentioned alcohol represented by General Formula (I) is subjected to the dehydration reaction in the presence of the above dehydration catalyst in a form of pure alcohol or in a form of crude alcohol which contains impurities. Here, the above-mentioned alcohol represented by General Formula (I) that is actually subjected to dehydration reaction in the presence of the above dehydration catalyst and may contain impurities may be called "raw material alcohol" in the present specification. Examples of such impurities that may be contained in the raw material alcohol include unreacted raw materials used for the production of the above-mentioned alcohol represented by General Formula (I) and by-products produced in the production step of the above-mentioned alcohol represented by General Formula (I). Further, as described later, alcohol in a form of containing water may be used as "raw material alcohol" in the present invention; and such an alcohol in a form of containing water is called "hydrous alcohol" regardless of the presence of the above-mentioned unreacted raw materials and other impurities such as by-products in the present specification. It is to be noted that, when the above-mentioned alcohol represented by General Formula (I) is called "pure alcohol" in the present specification, it refers to an alcohol that is only composed of the above-mentioned alcohol represented by General Formula (I).

A reaction temperature is not in particular restricted and is in a range of preferably 50 to 500° C. and more preferably 60 to 400° C. Further, a preferred applied pressure range is usually 0.1 to 500 atm and more preferably 0.5 to 100 atm.

The raw material alcohol used as the raw material of dehydration reaction in the present invention will be described in a little more detail.

As described above, the "raw material alcohol" that is actually subjected to the dehydration reaction in the presence of the above dehydration catalyst is not necessarily limited to a form of pure alcohol and may contain impurities. In a typical mode of the present invention, the above-mentioned alcohol represented by General Formula (I) obtained by hydrogenating a corresponding ketone is used as the raw material alcohol. In this case, the raw material alcohol used in the production method of the present invention may contain, in addition to the above-mentioned alcohol represented by General Formula (I), unreacted corresponding ketone. For example, in cases where isopropyl alcohol is used as the above-mentioned alcohol represented by General Formula (I), isopropyl alcohol that is obtained by hydrogenating acetone may be used as the raw material alcohol. And then, the raw material alcohol may contain, in addition to isopropyl alcohol, unreacted acetone and the like.

In this regard, according to the production method of the present invention, even in a system in which, based on 1 part by weight of alcohol represented by General Formula (I), 0.01 to 1 part by weight of corresponding ketone before hydrogenating to the alcohol coexists, that is, even in cases where a mixture containing 1 part by weight of the above-mentioned alcohol represented by General Formula (I) and 0.01 to 1 part by weight of corresponding ketone is used as the raw material alcohol, concurrence of side reactions such as aldol condensation of ketone can be minimized to proceed with the dehydration reaction of the above-mentioned alcohol represented by General Formula (I) with a high efficiency.

Further, the raw material alcohol used as the raw material of dehydration reaction in the present invention may contain water. This also applies to the case of using alcohol obtained by hydrogenating a corresponding ketone as the raw material alcohol, for example in the case of using isopropyl alcohol obtained by hydrogenating acetone as the raw material alcohol.

In this regard, in the production method of the present invention, even if water is contained in a reaction system, in particular, even if water is contained in the raw material alcohol, the dehydration reaction efficiently progresses, which is also one of the features of the present invention. As just described, in cases where the dehydration reaction progresses under the coexistence of water, the concentration of water in the system, typically the concentration of water in the raw material alcohol is usually 1 to 10% by weight, preferably 1 to 8% by weight, and more preferably 1 to 6% by weight. Even if water coexists in the raw material alcohol, the coexistence does not place particular burdens on a purification step after the reaction because water can be readily separated under normal pressure in the case of the formed olefin being gaseous.

When this is applied to, for example, the case in which isopropyl alcohol is used as the above-mentioned alcohol represented by General Formula (I), according to the production method of the present invention, it is possible for isopropyl alcohol to be subjected to the dehydration reaction in the presence of the above dehydration catalyst in a form of hydrous alcohol. In other words, in a preferred mode of the present invention, the dehydration catalyst composed of the above silica gel (X) can be used for propylene production by the dehydration reaction of hydrous isopropyl alcohol.

It is also possible for the dehydration reaction to be performed in a diluted condition by addition of a solvent or gas that is inert to the catalyst and the raw material to the reaction system.

When the invention is carried out, the process can be carried out by any of a batch process, a semibatch process, and a continuous flow process. It can be carried out in any form of a liquid phase, a gaseous phase, and a gas-liquid mixed phase. As a method of filling the catalyst, various methods such as fixed bed, fluid bed, suspension bed, and tray fixed bed are employed; and any of the methods may be allowed to carry out the filling.

Further, with regard to combination of catalysts filled, the catalyst of the present invention, that is, the dehydration catalyst composed of the above silica gel (X) may be solely filled to be used as the dehydration catalyst, or a general catalyst may be partially included. For example, as the reaction progresses, the content of water increases in the vicinity of the outlet of reactor; and therefore it is also useful to use the catalyst of the present invention in the latter half of the reactor.

In cases where the catalytic activity decreases when a certain amount of time passes, the activity of the above-mentioned dehydration catalyst can be recovered by carrying out regeneration by a known method.

For the purpose of maintaining the amount of the olefin produced, a merry-go-round system may be employed, wherein two or three reactors are arranged in parallel; and while the regeneration is carried out in one reactor, the reaction is carried out in the remaining one or two reactors. Further, incases where three reactors are used, a method of reducing changes in the production amount can be employed, wherein the other two reactors may be connected in series. In addition, in cases where the reaction is carried out by a fluidized bed flow reaction method or a moving bed reaction method, it is possible to continuously or intermittently take out all or part of the catalysts from the reactor and refill with an equivalent volume of them, thereby maintaining a constant activity.

Here, one of the parameters related to the amount of the olefin produced is LHSV (liquid hourly space velocity). In the present specification, LHSV is expressed as a liquid flow of raw material alcohol per the volume of the catalyst filled, for example, a volume ratio when isopropyl alcohol is flowed for one hour. Here, the larger the numerical value of LHSV is, the more volume of isopropyl alcohol flows, which increases the burden on the catalyst. The conversion therefore tends to decrease. In addition, as the conversion becomes higher, impurities are produced as by-products due to oligomerization and the selectivity tends to decrease. As just described, the numerical value of LHSV affects the reaction activity and selectivity. The invention of the present invention is in particular excellent in that an excellent reaction activity and selectivity are maintained even when LHSV is 2 or higher.

<Applications>

Applications of the olefin production method according to the present invention described above are not in particular restricted; and examples of typical applications include regeneration of propylene from acetone produced as a by-product upon phenol synthesis by the cumene process.

In the cumene process, benzene and propylene are subjected to an addition reaction to yield cumene. This cumene is oxidized to yield cumene hydroperoxide; and this cumene hydroperoxide is further subjected to acid cleavage, thereby giving phenol and acetone. Here, the regeneration of propylene from acetone can be carried out by subjecting acetone to a hydrogenation reaction to yield isopropyl alcohol, and further subjecting this isopropyl alcohol to a dehydration reaction. The thus regenerated propylene can again be reused for the phenol synthesis by the cumene process.

In this series of processes, the olefin production method according to the present invention described above can advantageously be applied to the regeneration of propylene from isopropyl alcohol obtained by the hydrogenation reaction of acetone. This is because conversion from isopropyl alcohol to propylene can efficiently be carried out even if isopropyl alcohol containing acetone or the like is used as the raw material alcohol used for the dehydration reaction of isopropyl alcohol.

With the above in mind, a cumene production method using propylene obtained by the olefin production method described above can be included as one of the applications of the present invention. Here, cumene can be obtained by subjecting benzene and propylene to an addition reaction by a conventional method such as the Friedel-Crafts reaction. The thus obtained cumene can be used as an intermediate raw material in the phenol synthesis by the cumene process.

EXAMPLES

By way of examples, the present invention will now be described in further detail; but the present invention is not limited thereto.

(Dehydration Catalysts Used in Examples)

As a silica gel used as a raw material of a silica gel (X), that is, a silica gel (A), the following silica that was commercially available from Fuji Silysia Chemical Ltd. was used. It is to be noted that each of the property values is a value listed in the catalog.

CARiACT Q-10; average fine pore diameter 10 nm, fine pore volume 1.0 ml/g, specific surface area 300 $m^2/g$ CARiACT Q-15; average fine pore diameter 15 nm, fine pore volume 1.0 ml/g, specific surface area 200 $m^2/g$ CARiACT Q-20; average fine pore diameter 20 nm, fine pore volume 1.0 ml/g, specific surface area 150 $m^2/g$ CARiACT Q-30; average fine pore diameter 30 nm, fine pore volume 1.0 ml/g, specific surface area 100 $m^2/g$ CARiACT Q-50; average fine pore diameter 50 nm, fine pore volume 1.0 ml/g, specific surface area 80 $m^2/g$

[Method for Evaluating Dehydration Catalyst]

(1) Amount of Aluminum Supported

The amount of aluminum supported in the silica gel (X) obtained in the example below was determined by subjecting each silica gel (X) to metal analysis by inductively coupled plasma (ICP) spectroscopy.

(2) Dehydration Reaction Performance

In order to evaluate the performance of a dehydration catalyst in a dehydration reaction of isopropyl alcohol (in the description hereinafter, may be abbreviated as IPA), a pressurized gas-phase downflow reaction was carried out using a fixed bed reaction apparatus which included a high pressure feed pump, a high pressure nitrogen mass flow controller, an electric furnace, a reactor having a catalyst-packing zone, and a back pressure valve.

One milliliter of a dehydration catalyst classified to sizes of 250 to 500 μm was filled in a SUS 316 reactor with an inner diameter of 1 cm. After the pressure was increased to 2.0 MPa with nitrogen, isopropyl alcohol was passed through the reactor at 300° C. under a stream of nitrogen at 10 ml/min from the inlet side of the reactor. The reaction was carried out while introducing nitrogen at 200 ml/min in the middle between the reactor outlet and the back pressure valve through the high pressure nitrogen mass flow controller.

It is to be noted that isopropyl alcohol, which is the raw material, was obtained by hydrogenation reaction of acetone; and one containing 0.4% by weight acetone and 4.7% by weight water was used. The activity of the catalyst was evaluated by comprehensively comparing the reaction results when LHSV was changed.

After the reaction settled into the steady state (usually after the passage of 20 hours from the initiation of liquid passage), the reaction gas and the reaction liquid were sampled from the exit side of the back pressure valve and were analyzed by GC. The reaction results were calculated to evaluate the catalyst.

Example 1

A 50 ml beaker was charged with 10.0 g of silica gel CARiACT (Q-10) manufactured by Fuji Silysia Chemical Ltd. and 25 g of a 1.39% by weight aqueous aluminum nitrate solution. These were left to stand at room temperature for one hour; and excess aqueous aluminum nitrate solution (about 15 g) with which the silica gel was not impregnated was removed by a filtration procedure. The residue was dried at 120° C. for three hours and calcined at 500° C. for six hours to give a silica gel (X) in which aluminum was supported in the amount of 1,000 ppm by weight as a dehydration catalyst according to the present invention. The catalytic performance in dehydration of the present catalyst was evaluated in accordance with the dehydration catalyst evaluation method. The results are described in Table 1.

Example 2

The same procedures as described in Example 1 were carried out except that Q-15 was used in place of the silica gel Q-10 and a 2.78% by weight aqueous aluminum nitrate solution was used in place of the 1.39% by weight aqueous aluminum nitrate solution, thereby giving a silica gel (X) in which aluminum was supported in the amount of 2,000 ppm by weight. The catalytic performance in dehydration of the present catalyst was evaluated in accordance with the dehydration catalyst evaluation method. The results are described in Table 1.

Example 3

The same procedures as described in Example 2 were carried out except that Q-20 was used in place of the silica gel Q-15 in Example 2, thereby giving a silica gel (X) in which aluminum was supported in the amount of 2,000 ppm by weight. The catalytic performance in dehydration of the present catalyst was evaluated in accordance with the dehydration catalyst evaluation method. The results are described in Table 1.

Example 4

The same procedures as described in Example 2 were carried out except that Q-30 was used in place of the silica gel Q-15 in Example 2, thereby giving a silica gel (X) in which aluminum was supported in the amount of 2,000 ppm by weight. The catalytic performance in dehydration of the present catalyst was evaluated in accordance with the dehydration catalyst evaluation method. The results are described in Table 1.

Example 5

The same procedures as described in Example 2 were carried out except that Q-50 was used in place of the silica gel Q-15 in Example 2, thereby giving a silica gel (X) in which aluminum was supported in the amount of 2,000 ppm by weight. The catalytic performance in dehydration of the present catalyst was evaluated in accordance with the dehydration catalyst evaluation method. The results are described in Table 1.

Comparative Example 1

The catalytic performance in dehydration of γ-alumina (N612N) manufactured by JGC Catalysts and Chemicals Ltd., which had been industrially used as a dehydration catalyst of alcohol, was evaluated in accordance with the dehydration catalyst evaluation method. The results are described in Table 1.

TABLE 1

| | Silica gel CARiACT | Concentration of Al supported (ppm by weight) | LHSV (1/h) | IPA conversion (mol %) | Propylene selectivity (mol %) |
|---|---|---|---|---|---|
| Example 1 | Q-10 | 1,000 | 1.1 | 99.7 | 98.8 |
| | | | 1.6 | 99.7 | 98.8 |
| | | | 2.0 | 96.6 | 98.6 |
| Example 2 | Q-15 | 2,000 | 1.2 | 99.9 | 98.0 |
| | | | 1.6 | 99.8 | 98.3 |
| | | | 2.0 | 99.8 | 98.8 |
| | | | 2.3 | 99.5 | 98.3 |
| Example 3 | Q-20 | 2,000 | 1.7 | 99.9 | 98.9 |
| | | | 2.0 | 99.9 | 98.9 |
| | | | 2.5 | 99.9 | 99.1 |
| | | | 3.1 | 99.0 | 99.1 |
| Example 4 | Q-30 | 2,000 | 1.6 | 99.8 | 98.9 |
| | | | 2.1 | 99.7 | 99.0 |
| | | | 2.5 | 99.5 | 99.1 |
| | | | 3.1 | 98.5 | 99.2 |
| Example 5 | Q-50 | 2,000 | 1.2 | 99.8 | 99.0 |
| | | | 1.6 | 99.6 | 99.2 |
| | | | 1.9 | 99.2 | 99.1 |
| Comparative Example 1 | γ-Al$_2$O$_3$ | | 1.0 | 99.8 | 99.2 |
| | | | 1.6 | 96.9 | 99.3 |
| | | | 2.0 | 89.0 | 98.0 |

As shown in Table 1, with γ-Al$_2$O$_3$, a dehydration catalyst of alcohol which has been industrially used so far, when LHSV is increased, the IPA conversion decreased. From this, an increase in the amount of IPA treated cannot be expected when LHSV is 1 or higher. By contrast, it is appreciated that when the catalyst in which alumina is supported onto the silica gel is used, IPA can be treated, while keeping the propylene selectivity high, with a high conversion even if LHSV is increased.

The numerical value following the letter Q of CARiACT manufactured by Fuji Silysia Chemical Ltd. refers to the average fine pore diameter (nm) of silica gel. The larger the value is, the larger the fine pore diameter is. When the amount of aluminum supported is identical, a larger average fine pore diameter results in a lower dehydration activity of the catalyst and a tendency of increased propylene selectivity is seen.

Example 6

The same procedures as described in Example 4 were carried out except that a 2.09% by weight aqueous aluminum nitrate solution was used in place of the 2.78% by weight aqueous aluminum nitrate solution in Example 4, thereby giving a silica gel (X) in which aluminum was supported in the amount of 1,500 ppm by weight. The catalytic performance in dehydration of the present catalyst was evaluated in accordance with the dehydration catalyst evaluation method. The results are described in Table 2.

Example 7

The same procedures as described in Example 5 were carried out except that a 4.17% by weight aqueous aluminum nitrate solution was used in place of the 2.78% by weight aqueous aluminum nitrate solution in Example 5, thereby giving a silica gel (X) in which aluminum was supported in the amount of 3,000 ppm by weight. The catalytic performance in dehydration of the present catalyst was evaluated in accordance with the dehydration catalyst evaluation method. The results are described in Table 2.

Example 8

The same procedures as described in Example 5 were carried out except that a 6.95% by weight aqueous aluminum nitrate solution was used in place of the 2.78% by weight aqueous aluminum nitrate solution in Example 5, thereby giving a silica gel (X) in which aluminum was supported in the amount of 5,000 ppm by weight. The catalytic performance in dehydration of the present catalyst was evaluated in accordance with the dehydration catalyst evaluation method. The results are described in Table 2.

TABLE 2

| | Silica gel CARiACT | Concentration of Al supported (ppm by weight) | LHSV (1/h) | IPA conversion (mol %) | Propylene selectivity (mol %) |
|---|---|---|---|---|---|
| Example 6 | Q-30 | 1,500 | 1.2 | 99.9 | 98.9 |
| | | | 1.6 | 99.8 | 99.0 |
| | | | 1.9 | 99.2 | 99.1 |
| | | | 2.5 | 98.4 | 99.0 |
| Example 4 | | 2,000 | 1.6 | 99.8 | 98.9 |
| | | | 2.1 | 99.7 | 99.0 |
| | | | 2.5 | 99.5 | 99.1 |
| | | | 3.1 | 98.5 | 99.2 |
| Example 5 | Q-50 | 2,000 | 1.2 | 99.8 | 99.0 |
| | | | 1.6 | 99.6 | 99.2 |
| | | | 1.9 | 99.2 | 99.1 |
| Example 7 | | 3,000 | 1.5 | 99.9 | 99.1 |
| | | | 1.9 | 99.3 | 99.1 |
| Example 8 | | 5,000 | 1.5 | 99.9 | 98.8 |
| | | | 1.9 | 99.9 | 98.7 |
| | | | 2.4 | 99.3 | 98.8 |
| | | | 3.0 | 99.1 | 99.0 |

As shown in Table 2, as the concentration of the aluminum supported is increased, the IPA conversion tends to become higher and the propylene selectivity tends to become lower. In the present catalyst system, an optimal silica gel and an optimal amount of the aluminum supported can be selected according to operating conditions.

INDUSTRIAL APPLICABILITY

According to the present invention, provided is a method of efficiently producing olefin such as propylene with a high activity and a high selectivity even in a high LHSV range through an intramolecular dehydration reaction of alcohol such as isopropyl alcohol by using a particular dehydration catalyst.

The invention claimed is:

1. An olefin production method, comprising producing an olefin represented by General Formula (II) below from an alcohol represented by General Formula (I) below using, as a dehydration catalyst, a chemically treated silica gel (X) in which an aluminum compound is supported onto a silica gel (A) with an average fine pore diameter of 10 to 50 nm in an amount of 1,000 to 10,000 ppm by weight in terms of aluminum element:

[Chem. 1]

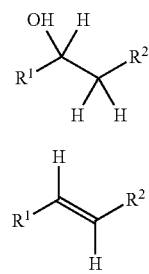

(in General Formulae (I) and (II), $R^1$ is selected from alkyl groups of 1 to 5 carbon atoms and $R^2$ is selected from a hydrogen atom and alkyl groups of 1 to 5 carbon atoms).

2. The olefin production method according to claim 1, wherein
the average fine pore diameter of the silica gel (A) is 20 to 50 nm and
the amount of the aluminum compound supported is more than 1,000 ppm by weight and not more than 10,000 ppm by weight in terms of aluminum element.

3. The production method according to claim 1, wherein the alcohol represented by the General Formula (I) is, in a form of a hydrous alcohol, subjected to a dehydration reaction in the presence of the dehydration catalyst.

4. The production method according to claim 3, wherein a content of water in the hydrous alcohol is 1 to 10% by weight.

5. The olefin production method according to claim 1, wherein the chemically treated silica gel (X) is a silica gel obtained by bringing the silica gel (A) into contact with a water-soluble aluminum compound and calcining the resulting product.

6. The olefin production method according to claim 1, wherein the alcohol represented by General Formula (I) is isopropyl alcohol and the olefin represented by General Formula (II) is propylene.

7. The olefin production method according to claim 1, wherein the dehydration reaction temperature is 50 to 500° C.

* * * * *